United States Patent [19]

Kameswaran

[11] Patent Number: 5,128,485

[45] Date of Patent: Jul. 7, 1992

[54] SYNTHESIS OF 2-ARYL-5-(TRIFLUOROMETHYL)PYR-ROLES USEFUL AS PESTICIDAL AGENTS AND AS INTERMEDIATES FOR THE PREPARATION OF SAID AGENTS

[75] Inventor: Venkataraman Kameswaran, Princeton Junction, N.J.

[73] Assignee: American Cyanamid Company, Stamford, Conn.

[21] Appl. No.: 628,751

[22] Filed: Dec. 17, 1990

[51] Int. Cl.$^5$ .................. C07D 207/34; C07D 207/42
[52] U.S. Cl. .................... 548/561; 548/526; 548/531; 548/557; 548/562; 548/563

[58] Field of Search ............ 548/531, 526, 557, 561, 548/562, 563

[56] References Cited

U.S. PATENT DOCUMENTS 4,333,878  6/1982  Dagani ........................ 548/531
5,010,098  4/1991  Brown et al. .................. 514/426

Primary Examiner—Patricia L. Morris

[57] ABSTRACT

There is provided a synthesis of 2-aryl-5-(trifluoromethyl)pyrrole compounds via the condensation of a suitable enamine with an α-haloketone.

8 Claims, No Drawings

SYNTHESIS OF 2-ARYL-5-(TRIFLUOROMETHYL)PYRROLES USEFUL AS PESTICIDAL AGENTS AND AS INTERMEDIATES FOR THE PREPARATION OF SAID AGENTS

BACKGROUND OF THE INVENTION

Arylpyrrole compounds are highly effective insecticidal, acaricidal and nematocidal agents.

It is an object of this invention to provide an effective single step formation of a wide variety of 2-aryl-5-(trifluoromethyl)pyrrole compounds.

SUMMARY OF THE INVENTION

The present invention is directed to a process for the preparation of arylpyrrole compounds of formula I $$\text{(I)}$$

[structure of formula I: aryl ring with substituents M, R, L attached to a pyrrole ring bearing W and $CF_3$, with N–A]

wherein

A is hydrogen, phenyl or $C_1$-$C_6$ alkyl optionally substituted with phenyl;

W is CN, $NO_2$, $CO_2R_1$ or $SO_2R_2$;

L is hydrogen or halogen;

M and R are each independently hydrogen, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, CN, $NO_2$, Cl, Br, F, I, $CF_3$, $R_3CF_2Z$, $R_4CO$ or $NR_5R_6$ and when M and R are on adjacent positions they may be taken together with the carbon atoms to which they are attached to form a ring in which MR represents the structure —$OCH_2O$—, —$OCF_2O$— or
—CH=CH—CH=CH—;

$R_1$ is $C_1$-$C_6$ alkyl, $C_3$-$C_6$ cycloalkyl or phenyl;
$R_2$ is $C_1$-$C_6$ alkyl, $C_3$-$C_6$ cycloalkyl or phenyl;
$R_3$ is hydrogen, F, $CHF_2$, CHFCl or $CF_3$;
$R_4$ is $C_1$-$C_4$ alkyl, $C_1$-$C_4$ alkoxy or $NR_5R_6$;
$R_5$ is hydrogen or $C_1$-$C_4$ alkyl;
$R_6$ is hydrogen, $C_1$-$C_4$ alkyl or $R_7CO$;
$R_7$ is hydrogen or $C_1$-$C_4$ alkyl;
Z is $S(O)_n$ or O and
n is an integer of 0, 1 or 2 which comprises reacting a compound of formula II $$\text{(II)}$$

[structure of formula II: aryl with M, R, L substituents, vinyl group bearing W, NH–A]

wherein A, W, L, M and R are described above with at least one molar equivalent of a compound of formula III $$CF_3-\overset{O}{\underset{\|}{C}}-CH_2X \quad \text{(III)}$$

wherein X is Cl, Br or I in the presence of an acid and a solvent.

The arylpyrrole compounds of formula I are highly useful as insecticidal, acaricidal and nematocidal agents and, further, are important intermediates in the manufacture of certain insecticidal arylpyrrole compounds. The utility is described in copending U.S. application Ser. No. 392,495, filed on Aug. 11, 1989, and Ser. No. 634,288, filed on Dec. 26, 1990, which are incorporated herein by reference thereto.

DESCRIPTION OF THE INVENTION

Surprisingly, it has been found that pyrrole rings substituted at the α-positions may be effectively prepared in a single step process via the condensation of a suitable enamine with an α-haloketone. Thus, pyrrole compounds of formula I may be prepared by reacting an enamine of formula II with about one molar equivalent of an α-haloketone of formula III in the presence of an acid and a solvent at preferably an elevated temperature. The reaction is illustrated in flow diagram I.

FLOW DIAGRAM I

[Structure II] + $CF_3-\overset{O}{\underset{\|}{C}}CH_2X$ ⟶ [Structure I]

II        III

I

The solvents suitable for use in the process of the present invention include organic solvents such as hydrocarbons and aromatic hydrocarbons having a boiling range of about 80° to 250° C., such as benzene, toluene, xylene and the like, preferably toluene. Acids suitable for use in the invention include organic acids such as acetic acid, propionic acid and the like, preferably acetic acid. Reaction temperatures of about 80° to 150° C. are suitable, with 90°-130° C. being preferred.

The compounds of formula II wherein A is hydrogen may be prepared by reacting the appropriate benzonitrile of formula IV with a compound of formula V in the presence of a base as shown in flow diagram II.

FLOW DIAGRAM II

[Structure IV: aryl with M, R, L substituents bearing C≡N] + $CH_3W$ $\xrightarrow{\text{base}}$

IV        V

-continued
FLOW DIAGRAM II

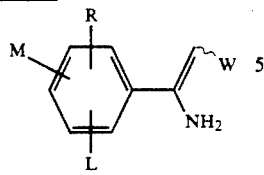

The compounds of formula II wherein A is other than hydrogen may be prepared by reacting the appropriate aroyl compound of formula VI with a suitable amine of formula VII as shown in flow diagram III.

FLOW DIAGRAM III

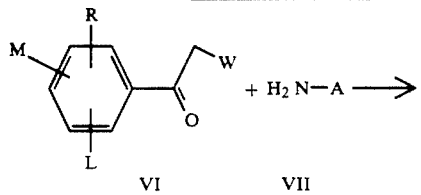

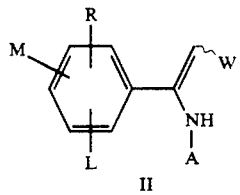

Arylpyrrole compounds of formula I may be useful as intermediates in the manufacture of insecticidal arylpyrroles. For example, compounds of formula I may be halogenated using a suitable halogenating agent such as a halogen, a hypohalite or the like to afford the corresponding 2-aryl-4-halopyrrole insecticidal agents of formula VIII. The reaction is shown in flow diagram IV.

FLOW DIAGRAM IV

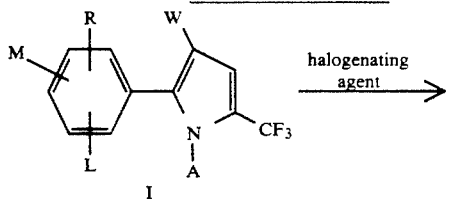

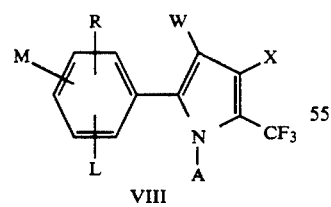

By varying the substituents, A, W, L, M and R and the halogen, X, numerous possible arylpyrroles may be prepared from the intermediate compounds of formula I.

In order to facilitate a further understanding of the present invention, the following examples are set forth primarily for the purpose of illustrating certain more specific details thereof. The invention is not to be limited, thereby except as defined in the claims. The terms IR and NMR designate infrared and nuclear magnetic resonance, respectively. The term HPLC designates high pressure liquid chromatography.

EXAMPLE 1

Preparation of 2-(3,4-Dichlorophenyl)-1-methyl-5-fluoromethyl)pyrrole-3-carbonitrile

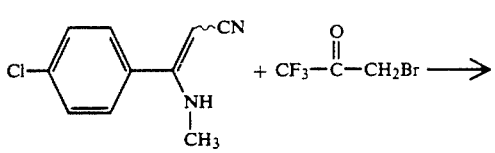

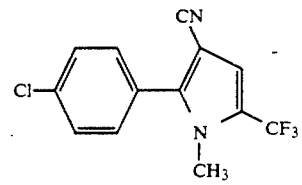

A solution of p-chloro-β-(methylamino)cinnaminitrile (10.0 g, 0.052 mol) in toluene and acetic acid is treated dropwise with 3-bromo-1,1,1-trifluoro-2-propanone (10.0 g, 0.052 mol) at room temperature, heated at reflux temperature for about 1 hour or until the disappearance of starting material by thin layer chromatography, cooled to room temperature and diluted with ethyl acetate. The organic phase is washed sequentially with water and 5N NaOH, dried (Na₂SO₄) and concentrated in vacuo to give a brown oil residue. The residue is flash chromatographed (silica gel, hexanes/-ethyl acetate, 80/20) to give the title product as a pale yellow solid 6.7 g (48% yield) mp 129.5° C. to 130.5° C., identified by IR and NMR spectral analyses.

EXAMPLE 2

Preparation of 2-(3,4-Dichlorophenyl)-1-methyl-5-(trifluoromethyl)-pyrrole-3-carbonitrile

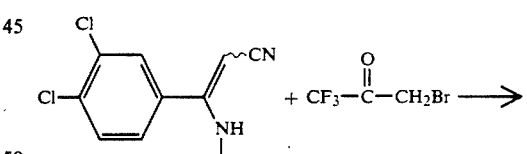

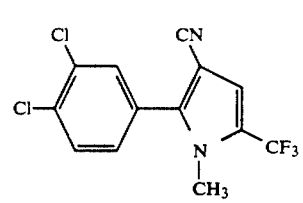

A solution of 3,4-dichloro-β-(methylamino)-cinnaminitrile (7.0 g, 0.031 mol) in toluene and acetic acid is treated dropwise with 3-bromo-1,1,1-trifluoro-2-propanone (6.0 g, 0.031 mol) at room temperature, heated at reflux temperature for 5 hours, cooled and diluted with ethyl acetate. The organic phase is washed sequentially with water and aqueous sodium hydroxide, dried (Na₂SO₄) and concentrated in vacuo to give a brown oil residue. The residue is flash chromatographed (silica gel, hexanes/ethyl acetate, 80/20) to give the title compound as a pale yellow solid, mp 130.2° C., identified by mass spectral, IR and NMR analyses.

EXAMPLE 3

Preparation of
1-Methyl-2-(2-naphthyl)-5-(trifluoromethyl)pyrrole-3-carbonitrile

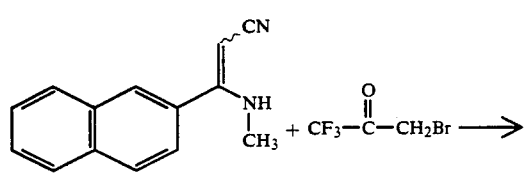

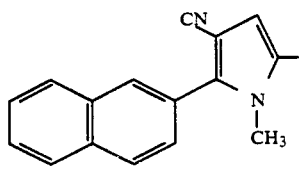

A solution of β-(methylamino)-2-naphthaleneacrylonitrile (2.5 g, 0.012 mol) in toluene and acetic acid is treated dropwise with 3-bromo-1,1,1-trifluoro-2-propanone (2.3 g, 0.012 mol) at room temperature, heated at reflux temperature for 6 hours, cooled and diluted with ethyl acetate. The organic phase is washed sequentially with water and 5N NaOH, dried (Na$_2$SO$_4$) and concentrated in vacuo to give a brown oil residue. The residue is flash chromatographed (silica gel, hexanes/ethyl acetate, 80/20) to give the title compound as a yellow solid, mp 134° C., identified by mass spectral, IR and NMR analyses.

EXAMPLE 4

Preparation of
2-(p-Chlorophenyl)-5-(trifluoromethyl)-pyrrole-3-carbonitrile

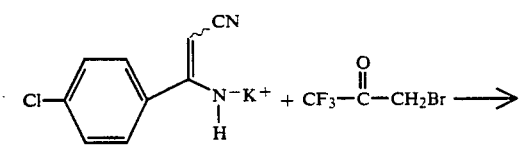

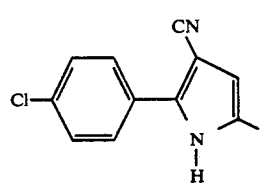

A mixture of β-amino-p-chlorocinnaminitrile potassium salt (2.2 g, 0.01 mol) in acetic acid is treated dropwise with 3-bromo-1,1,1-trifluoro-2-propanone (1.91 g, 0.01 mol) at room temperature, heated at 100° C. for 1½ hours, stirred at room temperature for 16 hours and diluted with water and ethyl acetate. The organic phase is washed sequentially with water and aqueous sodium hydroxide, dried (Na$_2$SO$_4$) and concentrated in vacuo to give a semi-solid residue. The residue is crystallized in ethyl acetate/heptane to give the title compound as a brown solid, mp 238° C. to 240° C., identified by $^{13}$C and $^1$HNMR analyses.

EXAMPLE 5

Preparation of
p-Chlorophenyl-β-(methylamino)cinnaminitrile

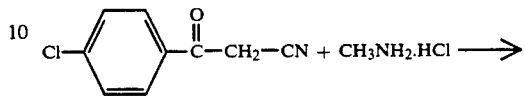

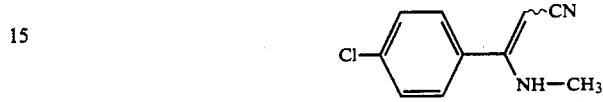

A mixture of p-chlorobenzoylacetonitrile (18.0 g, 0.1 mol), methylamine hydrochloride (10.13 g, 0.15 mol) and sodium acetate (12.3 g, 0.15 mol) in toluene is heated at reflux temperature (with a Dean Stark trap) for 5-6 hours, cooled to room temperature and diluted with water and ethyl acetate. The organic phase is separated and concentrated in vacuo to a residue which is crystallized from toluene/heptane to give the title product as a pale yellow solid, 17.1 g, (89% yield), mp 111.0° C. to 113.0° C., identified by $^{13}$C and $^1$HNMR spectral analyses.

EXAMPLE 6

Preparation of β-Amino-p-chlorocinnaminitrile,
potassium salt

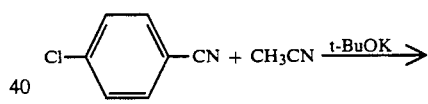

A solution of p-chlorobenzonitrile (13.8 g, 0.1 mol) in dimethoxyethane is treated with acetonitrile (4.93 g, 0.012 mol) at room temperature, treated portionwise with potassium t-butoxide (11.8 g, 0.105 mol), heated at reflux temperature for 1 hour, cooled to room temperature, diluted with ether and filtered. The solid filter cake is air dried and a 10 g sample is recrystallized from ethanol to give the title compound as a white solid, 3.9 g, identified by IR, $^{13}$C and $^1$HNMR spectral analyses.

EXAMPLE 7

Preparation of
β-(Methylamino)-2-naphthaleneacrylonitrile

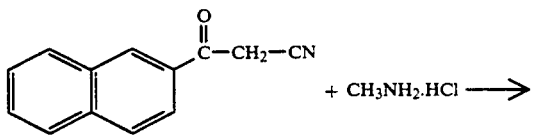

-continued

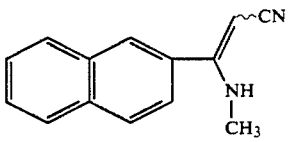

A solution of β-oxo-2-naphthalenepropionitrile (5.0 g, 0.0256 mol) in toluene is treated with methylamine hydrochloride ()2.6 g, 0.0384 mol), sodium acetate (3.15 g, 0.0386 mol) and a catalytic amount of acetic acid, heated at reflux temperature (fitted with a Dean Stark trap) for 6 hours, cooled, diluted with ethyl acetate and dilute hydrochloric acid. The organic phase is dried over $Na_2SO_4$ and concentrated in vacuo to give a residue which is triturated under hexanes to give the title compound as a yellow solid, 3.1 g (58% yield) mp 138° C., identified by IR, $^1$NHMR and mass spectral analyses.

EXAMPLE 8

Preparation of 2-p-(Chlorophenyl)-4-bromo-1-methyl-5-(trifluoromethyl)pyrrole-3-carbonitrile

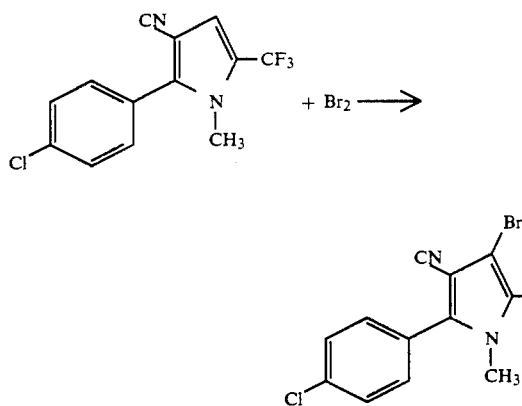

A solution of 2-(p-chlorophenyl)-1-methyl-5-(trifluoromethyl)pyrrole-3-carbonitrile (5.70 g, 0.02 mol) in chlorobenzene is treated with bromine (3.52 g, 0.022 mol), heated at 80° C. for 20 hours, cooled to room temperature, treated with additional bromine (3.52 g, 0.022 mol) and heated at 100° C. until reaction is complete by HPLC analysis. The reaction mixture is cooled to room temperature and diluted with ethyl acetate and water. The organic phase is washed with aqueous sodium metabisulfite, dried (MgSO4) and concentrated in vacuo to afford a solid residue. The residue is recrystallized from ethyl acetate/heptane to give the title product as a white solid, 6.50 g (89.4% yield), mp 126° C. to 129° C.

EXAMPLE 9

Preparation of 2-p-(Chlorophenyl)-4-chloro-5-(trifluoromethyl)pyrrole-3-carbonitrile

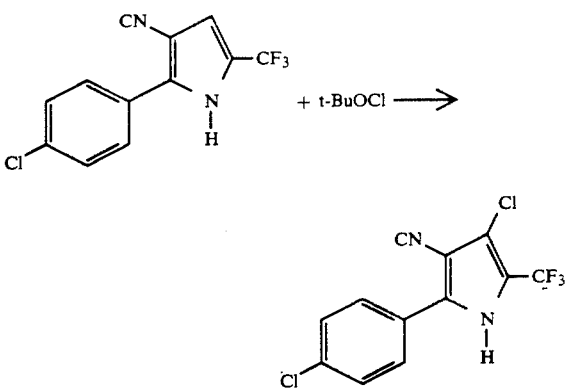

A solution of 2-(p-chlorophenyl)-5-(trifluoromethyl)-pyrrole-3-carbonitrile (20.0 g, 0.0739 mol) in monochlorobenzene is treated with t-butylhypochlorite (19.6 g, 0.087 mol), heated at 70° C. for 2 hours, treated with additional t-butylhypochlorite (2.0 g, 0.009 mol), heated at 80° C. to 82° C. for 1 hour, cooled to room temperature, diluted with heptane and filtered. The filter cake is air-dried to give the title product as a pale solid, 18.5 g, (82.5% yield), mp 242.5° C. to 243.0° C., identified by $^{19}$F and $^1$HNMR spectral analyses.

I claim:
1. A process for the preparation of a compound of formula I

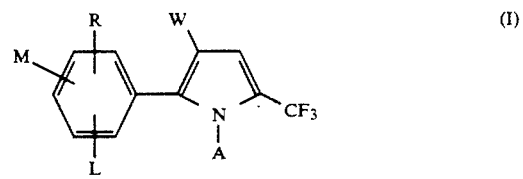

wherein
A is hydrogen, phenyl or $C_1-C_6$ alkyl optionally substituted with phenyl;
W is CN, $NO_2$, $CO_2R_1$ or $SO_2R_2$;
L is hydrogen or halogen;
M and R are each independently hydrogen, $C_1-C_4$ alkyl, $C_1-C_4$ alkoxy, $C_1-C_4$ alkylthio, $C_1-C_4$ alkylsulfinyl, $C_1-C_4$ alkylsulfonyl, CN, $NO_2$, Cl, Br, F, I, $CF_3$, $R_3CF_2Z$, $R_4CO$ or $NR_5R_6$ and when M and R are on adjacent positions they may be taken together with the carbon atoms to which they are attached to form a ring in which MR represents the structure —$OCH_2O$—, —$OCF_2O$— or
—CH=CH—CH=CH—;

$R_1$ is $C_1-C_6$ alkyl, $C_3-C_6$ cycloalkyl or phenyl;
$R_2$ is $C_1-C_6$ alkyl, $C_3-C_6$ cycloalkyl or phenyl;
$R_3$ is hydrogen, F, $CHF_2$, CHFCl or $CF_3$;
$R_4$ is $C_1-C_4$ alkyl, $C_1-C_4$ alkoxy or $NR_5R_6$;
$R_5$ is hydrogen or $C_1-C_4$ alkyl;
$R_6$ is hydrogen, $C_1-C_4$ alkyl or $R_7CO$;
$R_7$ is hydrogen or $C_1-C_4$ alkyl;

Z is S(O)$_n$ or O and n is an integer of 0, 1 or 2 which comprises reacting at a suitable temperature a compound of formula II

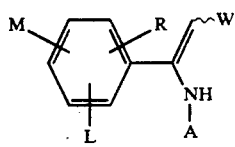

(II)

wherein A, W, L, M and R are described above with about one molar equivalent of a compound of formula III

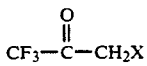

(III)

wherein X is Cl, Br or I in the presence of an acid and a solvent.

2. The process according to claim 1 wherein the reaction takes place at an elevated temperature.

3. The process according to claim 2 wherein the elevated temperature is about 90° C. to 130° C.

4. The process according to claim 1 wherein the acid is acetic acid.

5. The process according to claim 1 wherein W is CN.

6. The process according to claim 1 wherein W is NO$_2$.

7. The process according to claim 5 wherein A is hydrogen or methyl, L and R are hydrogen and M is halogen.

8. The process according to claim 5 wherein A is hydrogen or methyl, L is hydrogen and M and R are halogen.

* * * * *